(12) United States Patent
Hirota et al.

(10) Patent No.: US 11,103,137 B2
(45) Date of Patent: Aug. 31, 2021

(54) PHOTOACOUSTIC IMAGING METHOD AND DEVICE

(71) Applicant: FUJIFILM Corporation, Tokyo (JP)

(72) Inventors: Kazuhiro Hirota, Ashigarakami-gun (JP); Kazuhiro Tsujita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 754 days.

(21) Appl. No.: 15/958,210

(22) Filed: Apr. 20, 2018

(65) Prior Publication Data

US 2018/0235477 A1     Aug. 23, 2018

Related U.S. Application Data

(60) Division of application No. 14/457,921, filed on Aug. 12, 2014, now Pat. No. 9,974,439, which is a
(Continued)

(30) Foreign Application Priority Data

Feb. 13, 2012  (JP) ................................ 2012-028572
Jan. 24, 2013   (JP) ................................ 2013-010856

(51) Int. Cl.
*A61B 5/00* (2006.01)
*A61B 8/00* (2006.01)

(52) U.S. Cl.
CPC .......... *A61B 5/0095* (2013.01); *A61B 8/4416* (2013.01); *A61B 8/463* (2013.01)

(58) Field of Classification Search
None
See application file for complete search history.

(56) References Cited

U.S. PATENT DOCUMENTS 6,979,292 B2    12/2005   Kanayama et al.
2007/0179365 A1  8/2007   Bitton et al.
(Continued)

FOREIGN PATENT DOCUMENTS

JP    2005-021380 A    1/2005
JP    2011-217767 A1   11/2011
(Continued)

OTHER PUBLICATIONS

Chinese Office Action and Search Report, dated Jul. 24, 2015, for Chinese Application No. 201380009261.3, along with an English translation of the Chinese Office Action.
(Continued)

*Primary Examiner* — Jonathan Cwern
(74) *Attorney, Agent, or Firm* — Birch, Stewart, Kolasch & Birch, LLP

(57) ABSTRACT

A photoacoustic imaging method is provided that can prevent the surface of the subject from appearing in an image when a part to be observed at a position deeper than the surface of the subject is imaged. The photoacoustic imaging device includes a unit for outputting pulsed light toward the subject, and generating photoacoustic data by detecting photoacoustic waves emitted from the subject exposed to the light. The photoacoustic imaging device also includes a region detection unit that detects a near-surface region of the subject based on the photoacoustic wave detection signals, and a correcting unit that attenuates (which encompasses removing) information of the near-surface region found by the region detection unit when the part to be observed is displayed.

6 Claims, 9 Drawing Sheets

Related U.S. Application Data continuation of application No. PCT/JP2013/000675, filed on Feb. 7, 2013.

(56) References Cited

U.S. PATENT DOCUMENTS

| | | | |
|---|---|---|---|
| 2008/0319317 A1 | 12/2008 | Kamiyama et al. |
| 2010/0070233 A1 | 3/2010 | Masumura |
| 2010/0094561 A1 | 4/2010 | Masumura |
| 2011/0282181 A1 | 11/2011 | Wang et al. |
| 2012/0130222 A1 | 5/2012 | Kobayashi et al. |
| 2012/0296192 A1 | 11/2012 | Fukutani |

FOREIGN PATENT DOCUMENTS

| | | | |
|---|---|---|---|
| JP | 2012-024460 A | 2/2012 |
| WO | WO 2011/121977 A1 | 10/2011 |
| WO | WO 2012/014391 A1 | 2/2012 |

OTHER PUBLICATIONS

International Search Report issued in PCT/JP2013/000675 dated Apr. 16, 2013.

Wang et al., "A High-Speed Photoacoustic Tomography System based on a Commercial Ultrasound and a Custom Transducer Array", Proc. of SPIE, vol. 7564, 756424-1 to 756424-9, 2010.

Written Opinion of the International Searching Authority issued in PCT/JP2013/000675 dated Apr. 16, 2013.

Advisory Action dated Dec. 1, 2017 in copending U.S. Appl. No. 14/457,921.

Notice of Allowance dated Jan. 23, 2018 in copending U.S. Appl. No. 14/457,921.

Office Action dated Aug. 21, 2017 in copending U.S. Appl. No. 14/457,921.

Office Action dated Dec. 9, 2016 in copending U.S. Appl. No. 14/457,921.

Office Action dated Mar. 30, 2017 in copending U.S. Appl. No. 14/457,921.

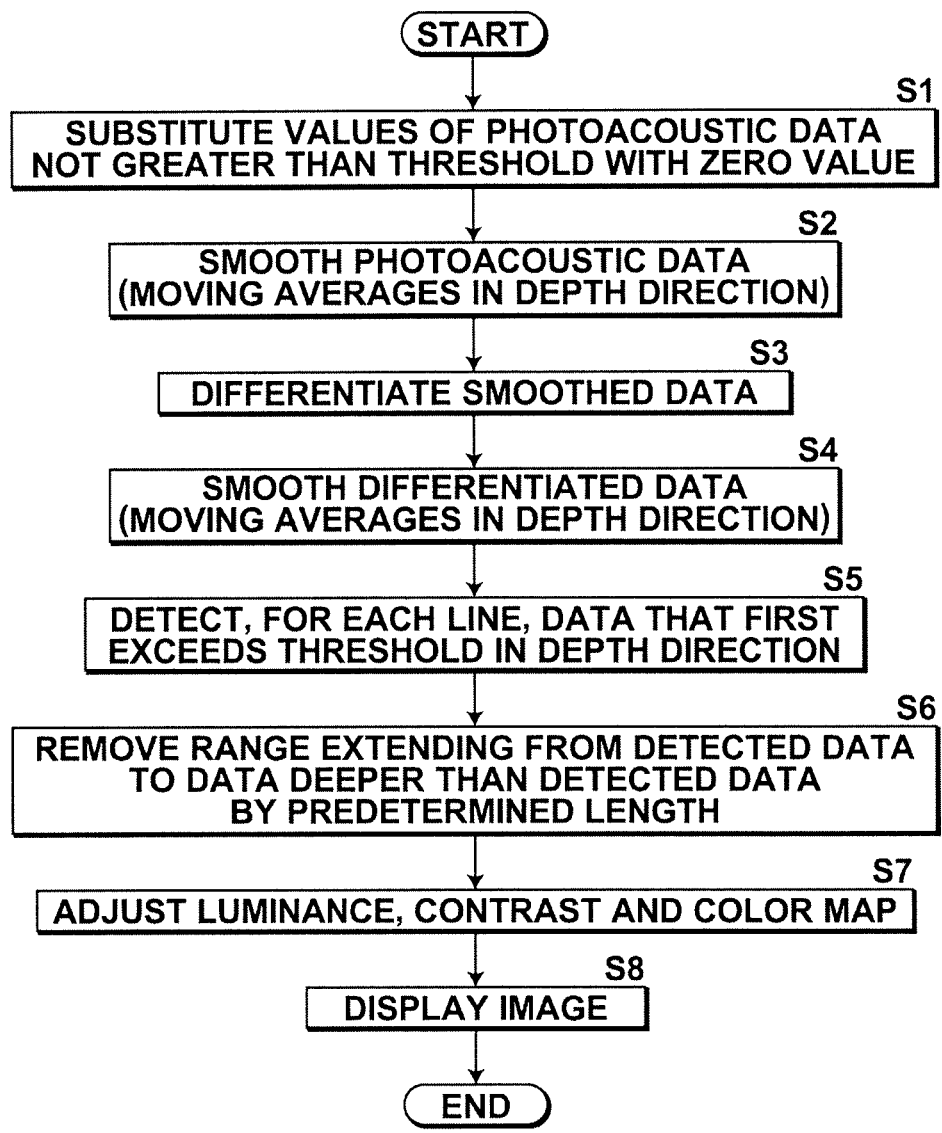

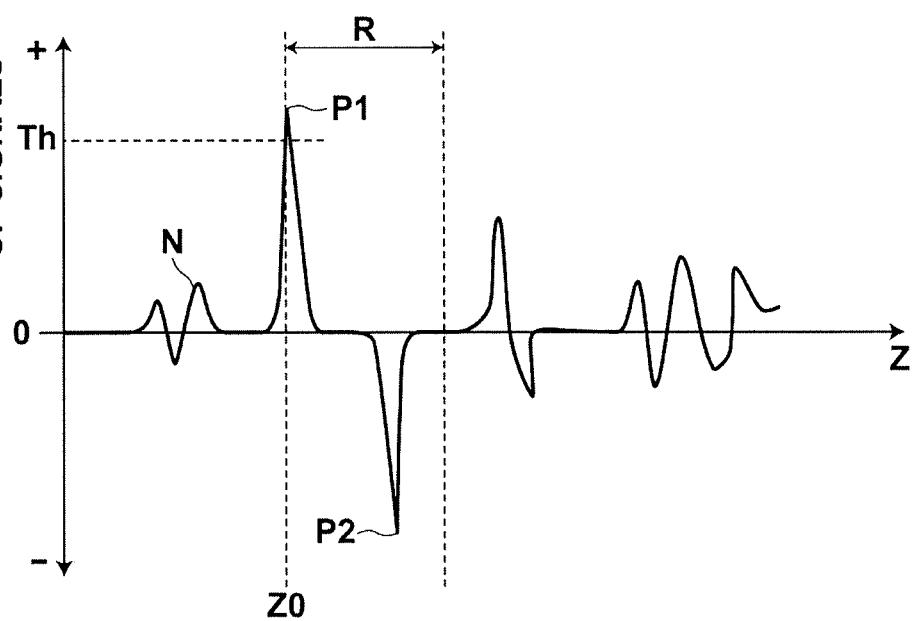

PHOTOACOUSTIC IMAGING METHOD AND DEVICE

CROSS-REFERENCE TO RELATED APPLICATIONS

This application is a Divisional of copending U.S. application Ser. No. 14/457,921 filed Aug. 12, 2014, which is a Continuation of PCT International Application No. PCT/JP2013/000675 filed on Feb. 7, 2013, which claims priority under 35 U.S.C. § 119(a) to Japanese Patent Application No. 2012-028572 filed on Feb. 13, 2012 and Japanese Patent Application No. 2013-010856 filed on Jan. 24, 2013. Each of the above applications is hereby expressly incorporated by reference, in its entirety, into the present application.

BACKGROUND OF THE INVENTION

Technical Field

The present invention relates to a photoacoustic imaging method, namely, a method for imaging a subject, such as a living tissue, based on photoacoustic waves emitted from the subject when it is exposed to light outputted toward the subject.

The present invention also relates to a device that carries out the photoacoustic imaging method.

Background Art

As disclosed in Japanese Unexamined Patent Publication Nos. 2005-021380 and 2011-217767 (hereinafter, Patent Documents 1 and 2, respectively) and X. Wang et al., "A High-Speed Photoacoustic Tomography System based on a Commercial Ultrasound and a Custom Transducer Array", Proc. of SPIE, Vol. 7564, pp. 756424-1-756424-9, 2010 (hereinafter, Non-Patent Document 1), for example, a photoacoustic imaging device for imaging the interior of a living body using the photoacoustic effect is conventionally known. With the photoacoustic imaging device, pulsed light, such as pulsed laser light, is outputted toward the living body. In the interior of the living body exposed to the pulsed light, a living tissue absorbs the energy of the pulsed light and the volume of the living tissue expands due to heat, and acoustic waves (photoacoustic waves) are emitted. By detecting the photoacoustic waves with a detection means, such as an ultrasound probe, the interior of the living body can be visualized based on the obtained electric signals (photoacoustic signals).

The photoacoustic imaging device constructs an image based only on photoacoustic waves emitted from specific absorptive substances, and is therefore suitable for imaging a specific tissue, such as blood vessels, in a living body.

With the photoacoustic imaging device, a tissue at a deeper position than the surface of the subject, such as blood vessels of a living body, can be imaged, as described above. To this end, it is necessary to set a relatively high intensity of the pulsed light so that the pulsed light can reach deep positions. In this case, however, near-surface parts of the subject (such as the epidermis and the body hair) exposed to the pulsed light emit photoacoustic waves, and a photoacoustic image of the near-surface parts may be generated and displayed. The thus displayed near-surface parts may hinder observation of an intended part to be observed, such as blood vessels, or may even hide the part to be observed.

Patent Document 1 also discloses a method for solving this problem. This method involves applying a Fourier transform in the spatial direction to photoacoustic wave detection signals obtained with a plurality of detection elements to cut off spatial low-frequency components, applying an inverse Fourier transform to the signals, and generating and displaying a photoacoustic image using the thus converted image signals.

DISCLOSURE OF THE INVENTION

The method disclosed in Patent Document 1, however, has a problem that a part to be observed, such as blood vessels, extending in a direction parallel to a direction in which the detection elements are arranged is also removed. This method also has a problem that, in a case where a probe that holds the detection elements is not pressed against the subject and the surface of the subject is not parallel to the direction in which the detection elements are arranged, that is, where the detection elements are used in a state where they are not in direct contact with the subject in water or in a gel-like material, for example, or there is a transparent substance on the surfaces of the detection elements, the effect of removing the surface of the subject is not sufficient.

In view of the above-described circumstances, the present invention is directed to providing a photoacoustic imaging method that can reliably prevent a near-surface part of the subject from being clearly imaged.

The present invention is also directed to providing a photoacoustic imaging device that is capable of carrying out the photoacoustic imaging method.

A first aspect of the photoacoustic imaging method according to the invention is a photoacoustic imaging method comprising: outputting light from a light source toward a part to be observed in a subject through a surface of the subject; obtaining photoacoustic wave detection signals by detecting photoacoustic waves emitted from the part to be observed exposed to the light; imaging the part to be observed based on the photoacoustic wave detection signals and displaying the part to be observed on an image display means; detecting a near-surface region of the subject based on the photoacoustic wave detection signals; and attenuating information of the near-surface region when the part to be observed is displayed.

The description "attenuating information of the near-surface region when . . . is displayed" encompasses removing the information in a case where the maximum degree of attenuation is applied (the same applies to the following description).

In the first aspect of the photoacoustic imaging method, more specifically, the photoacoustic wave detection signals are detected with respect to a region extending from the surface of the subject toward a depth direction of the subject, and a region extending between a position where a first extremum of differential values of the photoacoustic wave detection signals is found and a position where a next extremum of the differential values is found may be detected as the near-surface region.

Alternatively, in the first aspect of the photoacoustic imaging method, more specifically, the photoacoustic wave detection signals are detected with respect to a region extending from the surface of the subject toward a depth direction of the subject, and a region extending between a position where a first extremum of differential values of the photoacoustic wave detection signals is found and a position apart from the position where the first extremum is found by a predetermined length in the depth direction of the subject may be detected as the near-surface region.

Still alternatively, in the first aspect of the photoacoustic imaging method, more specifically, the photoacoustic wave detection signals are detected with respect to a region extending from the surface of the subject toward a depth direction of the subject, and a region extending between a position where a differential value of the photoacoustic wave detection signal that first exceeds a predetermined threshold value is found and a position where, after a first extremum of the differential values is found after the predetermined threshold value is exceeded, a next extremum of differential values of the photoacoustic wave detection signals is found may be detected as the near-surface region.

Yet alternatively, in the first aspect of the photoacoustic imaging method, more specifically, the photoacoustic wave detection signals are detected with respect to a region extending from the surface of the subject toward a depth direction of the subject, and a region extending between a position where a differential value of the photoacoustic wave detection signal that first exceeds a predetermined threshold value is found and a position apart from the position where the differential value that first exceeds the predetermined threshold value is found by a predetermined length in the depth direction of the subject may be detected as the near-surface region.

Yet alternatively, in the first aspect of the photoacoustic imaging method, more specifically, the photoacoustic wave detection signals are detected with respect to a region extending from the surface of the subject toward a depth direction of the subject, and a region extending between a position where a first extremum of differential values of the photoacoustic wave detection signals is found after a differential value of the photoacoustic wave detection signal that first exceeds a predetermined threshold value is found and a position where a next extremum of the differential values is found may be detected as the near-surface region.

Yet alternatively, in the first aspect of the photoacoustic imaging method, more specifically, the photoacoustic wave detection signals are detected with respect to a region extending from the surface of the subject toward a depth direction of the subject, and a region extending between a position where a first extremum of differential values of the photoacoustic wave detection signals is found after a differential value of the photoacoustic wave detection signal that first exceeds a predetermined threshold value is found and a position apart from the position where the first extremum is found by a predetermined length in the depth direction of the subject may be detected as the near-surface region.

In the first aspect of the photoacoustic imaging method, it is desirable that smoothing processing be applied to the photoacoustic wave detection signals before the differential values of the photoacoustic wave detection signals are calculated.

In the first aspect of the photoacoustic imaging method, it is desirable that smoothing processing be applied to the differential values used in processing for detecting the near-surface region before the processing for detecting the near-surface region is performed.

A second aspect of the photoacoustic imaging method according to the invention is a photoacoustic imaging method comprising: outputting light from a light source toward a part to be observed in a subject through a surface of the subject; obtaining photoacoustic wave detection signals by detecting photoacoustic waves emitted from the part to be observed exposed to the light; imaging the part to be observed based on the photoacoustic wave detection signals and displaying the part to be observed on an image display means; outputting acoustic waves toward the part to be observed through the surface of the subject, and obtaining reflected acoustic wave detection signals by detecting reflected acoustic waves reflected from the subject; detecting a near-surface region of the subject based on the reflected acoustic wave detection signals; and attenuating information of the near-surface region when the part to be observed is displayed.

In the second aspect of the photoacoustic imaging method, more specifically, the reflected acoustic wave detection signals are detected with respect to a region extending from the surface of the subject toward a depth direction of the subject, and a region extending between a position where the reflected acoustic wave detection signal begins to increase from a minimum value and a position where a first local maximum value of the reflected acoustic wave detection signals is found may be detected as the near-surface region.

Alternatively, in the second aspect of the photoacoustic imaging method, more specifically, the reflected acoustic wave detection signals are detected with respect to a region extending from the surface of the subject toward a depth direction of the subject, and a region extending between two positions that are apart from a position where an average value between a minimum value of the reflected acoustic wave detection signals and a first detected local maximum value of the reflected acoustic wave detection signals is found by a predetermined length in the depth direction of the subject and a predetermined length in an opposite direction from the depth direction of the subject may be detected as the near-surface region.

Further, it is more preferred that the photoacoustic imaging method of the invention be applied to a case where the light outputted toward the subject has a wavelength in the range from 700 to 850 nm.

A first aspect of the photoacoustic imaging device according to the invention is a photoacoustic imaging device comprising: a light source that emits light toward a part to be observed in a subject through a surface of the subject; a photoacoustic wave detection means that obtains photoacoustic wave detection signals by detecting photoacoustic waves emitted from the part to be observed exposed to the light; an image display means that images the part to be observed based on the photoacoustic wave detection signals and displays the part to be observed;

a means that detects a near-surface region of the subject based on the photoacoustic wave detection signals; and a correcting means that attenuates information of the near-surface region when the part to be observed is displayed.

In the first aspect of the photoacoustic device according to the invention, the photoacoustic wave detection signals are detected with respect to a region extending from the surface of the subject toward a depth direction of the subject, and, as the means that detects a near-surface region, for example, one that detects, as the near-surface region, a region extending between a position where a first extremum (a local maximum value or a local minimum value) of differential values of the photoacoustic wave detection signals is found and a position where a next extremum of the differential values is found may be applied.

Alternatively, the photoacoustic wave detection signals are detected with respect to a region extending from the surface of the subject toward a depth direction of the subject, and, as the means that detects a near-surface region, one that detects, as the near-surface region, a region extending between a position where a first extremum of differential values of the photoacoustic wave detection signals is found and a position apart from the position where the first extremum is found by a predetermined length in the depth direction of the subject may be applied.

Still alternatively, the photoacoustic wave detection signals are detected with respect to a region extending from the surface of the subject toward a depth direction of the subject, and, as the means that detects a near-surface region, one that detects, as the near-surface region, a region extending between a position where a differential value of the photoacoustic wave detection signal that first exceeds a predetermined threshold value is found and a position where a first extremum of differential values of the photoacoustic wave detection signals is found after the differential value that first exceeds the predetermined threshold value is found may be applied.

Yet alternatively, the photoacoustic wave detection signals are detected with respect to a region extending from the surface of the subject toward a depth direction of the subject, and, as the means that detects a near-surface region, one that detects, as the near-surface region, a region extending between a position where a differential value of the photoacoustic wave detection signal that first exceeds a predetermined threshold value is found and a position apart from the position where the differential value that first exceeds the predetermined threshold value is found by a predetermined length in the depth direction of the subject may be applied.

Yet alternatively, the photoacoustic wave detection signals are detected with respect to a region extending from the surface of the subject toward a depth direction of the subject, and, as the means that detects a near-surface region, one that detects, as the near-surface region, a region extending between a position where a first extremum of differential values of the photoacoustic wave detection signals is found after a differential value of the photoacoustic wave detection signal that first exceeds a predetermined threshold value is found and a position where a next extremum is found may be applied.

Yet alternatively, the photoacoustic wave detection signals are detected with respect to a region extending from the surface of the subject toward a depth direction of the subject, and, as the means that detects a near-surface region, one that detects, as the near-surface region, a region extending between a position where a first extremum of differential values of the photoacoustic wave detection signals is found after a differential value of the photoacoustic wave detection signal that first exceeds a predetermined threshold value is found and a position apart from the position where the first extremum is found by a predetermined length in the depth direction of the subject may be applied.

It is desirable that the first aspect of the photoacoustic device according to the invention comprise a means that applies smoothing processing to the photoacoustic wave detection signals before the differential values of the photoacoustic wave detection signals are calculated.

It is desirable that the first aspect of the photoacoustic device according to the invention comprise a means that applies smoothing processing to the differential values used in processing for detecting the near-surface region before the processing for detecting the near-surface region is performed.

A second aspect of the photoacoustic imaging device according to the invention is a photoacoustic imaging device comprising: a light source that emits light toward a part to be observed in a subject through a surface of the subject; a photoacoustic wave detection means that obtains photoacoustic wave detection signals by detecting photoacoustic waves emitted from the part to be observed exposed to the light; an image display means that images the part to be observed based on the photoacoustic wave detection signals and displays the part to be observed; a means that outputs acoustic waves toward the part to be observed through the surface of the subject; a reflected acoustic wave detection means that obtains reflected acoustic wave detection signals by detecting reflected acoustic waves reflected from the subject; a means that detects a near-surface region of the subject based on the reflected acoustic wave detection signals; and a correcting means that attenuates information of the near-surface region when the part to be observed is displayed.

In the second aspect of the photoacoustic imaging device according to the invention, the reflected acoustic wave detection signals are detected with respect to a region extending from the surface of the subject toward a depth direction of the subject, and, as the means that detects a near-surface region, one that detects, as the near-surface region, a region extending between a position where the reflected acoustic wave detection signal begins to increase from a minimum value and a position where a first local maximum value of the reflected acoustic wave detection signals is found may be applied.

Alternatively, the reflected acoustic wave detection signals are detected with respect to a region extending from the surface of the subject toward a depth direction of the subject, and, as the means that detects a near-surface region, one that detects, as the near-surface region, a region extending between two positions that are apart from a position where an average value between a minimum value of the reflected acoustic wave detection signals and a first detected local maximum value of the reflected acoustic wave detection signals is found by a predetermined length in a depth direction of the subject and a predetermined length in an opposite direction from the depth direction of the subject may be applied.

In the photoacoustic imaging device of the invention, it is more preferred that, as the light source, one that emits light having a wavelength in the range from 700 to 850 nm be used.

According to the first aspect of the photoacoustic imaging method of the invention, the near-surface region of the subject is found based on the photoacoustic wave detection signals, and information of the near-surface region is attenuated when the part to be observed is displayed. This allows reliably preventing the near-surface part of the subject from being clearly imaged. The present inventors have found through a study that the phenomenon where the near-surface part of the subject is imaged tends to occur when the light outputted toward the subject has a wavelength in the range from about 700 to 850 nm. Therefore, it is particularly effective to apply the method of the invention to the case where light having a wavelength in the above-described range is used.

Further, according to the second aspect of the photoacoustic imaging method of the invention, acoustic waves are outputted toward the part to be observed through the surface of the subject, reflected acoustic wave detection signals are obtained by detecting reflected acoustic waves reflected from the subject, the near-surface region of the subject is detected based on the reflected acoustic wave detection signals, and information of the near-surface region is attenuated when the part to be observed is displayed. This also allows reliably preventing the near-surface part of the subject from being clearly imaged.

The first aspect of the photoacoustic device of the invention includes the means that detects the near-surface region of the subject based on the photoacoustic wave detection signals, and the correcting means that attenuates information of the near-surface region when the part to be observed is displayed. Therefore, the device can carry out the above-described first aspect of the photoacoustic imaging method according to the invention.

The second aspect of the photoacoustic imaging device according to the invention includes the means that outputs acoustic waves toward the part to be observed through the surface of the subject, the reflected acoustic wave detection means that obtains reflected acoustic wave detection signals by detecting reflected acoustic waves reflected from the subject, the means that detects a near-surface region of the subject based on the reflected acoustic wave detection signals, and the correcting means that attenuates information of the near-surface region when the part to be observed is displayed. Therefore, the device can carry out the above-described second aspect of the photoacoustic imaging method according to the invention.

BRIEF DESCRIPTION OF THE DRAWINGS

FIG. 11 is a flow chart illustrating the flow of part of processing performed by the device shown in FIG. 10, and FIG. 12 is a schematic diagram for explaining a method for detecting the near-surface region of the subject with the device shown in FIG. 10.

DESCRIPTION OF PREFERRED EMBODIMENTS

Figure 1:
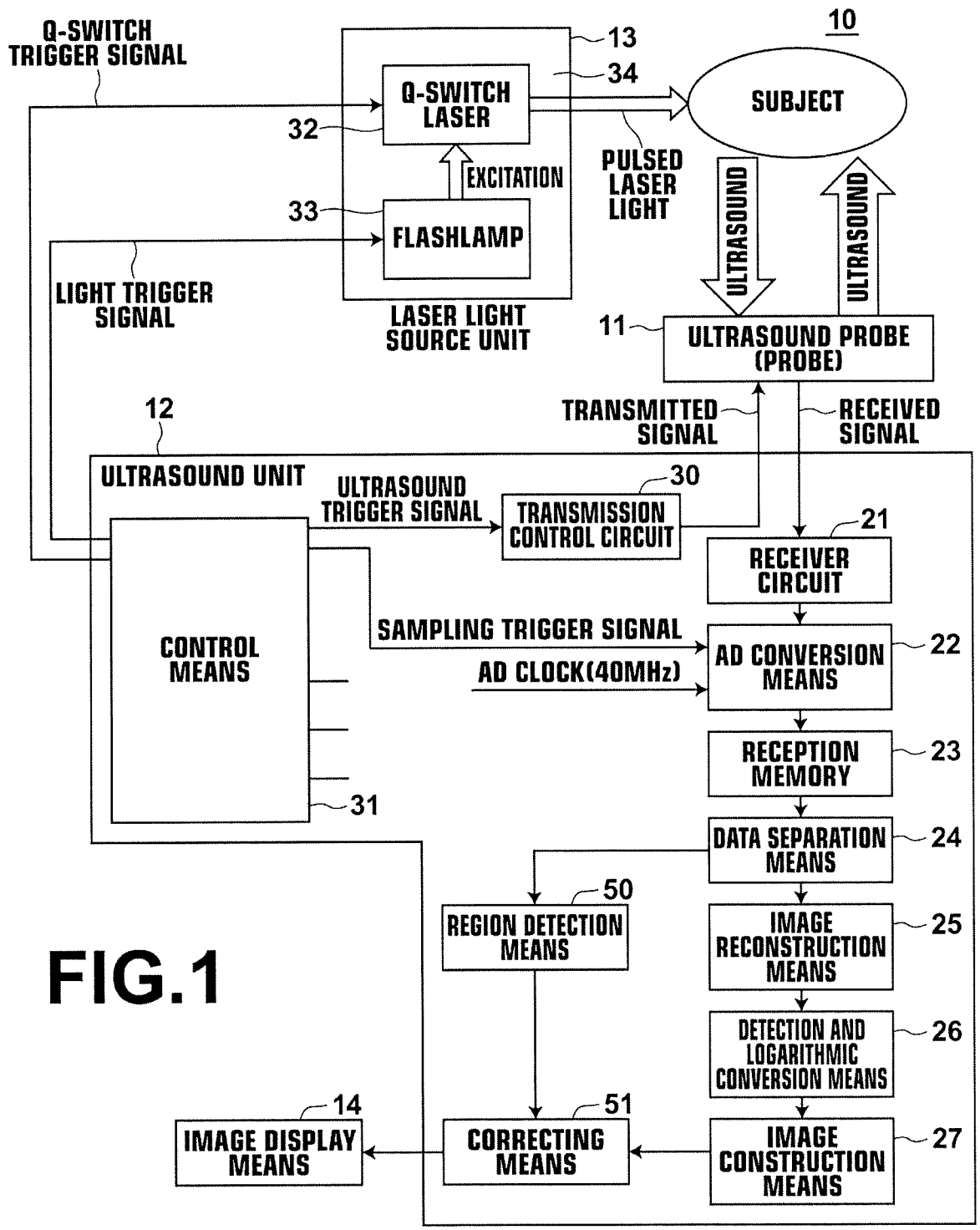
FIG. 1 is a block diagram illustrating the schematic configuration of a photoacoustic imaging device according to one embodiment of the invention.

Hereinafter, embodiments of the present invention will be described in detail with reference to the drawings. FIG. 1 is a block diagram illustrating the basic configuration of a photoacoustic imaging device 10 according to one embodiment of the invention. As one example, the photoacoustic imaging device 10 is capable of obtaining both a photoacoustic image and an ultrasound image, and includes an ultrasound probe 11, an ultrasound unit 12, a laser light source unit 13, and an image display means 14.

The laser light source unit 13 emits laser light with a center wavelength of 756 nm, for example. The laser light source unit 13 outputs the laser light toward the subject. It is desirable that the laser light be guided to the probe 11 with a light guide means, such as a plurality of optical fibers, and be outputted toward the subject from a part of the probe 11.

The probe 11 outputs (transmits) ultrasound toward the subject and detects (receives) reflected ultrasound that is reflected from the subject and returns to the probe 11. To this end, the probe 11 includes a plurality of ultrasound transducers, which are one-dimensionally arranged, for example. Further, the probe 11 detects, with the ultrasound transducers, ultrasound (photoacoustic waves) emitted from a part to be observed in the subject that has absorbed the laser light from the laser light source unit 13. The probe 11 detects the photoacoustic waves and outputs photoacoustic wave detection signals, and also detects the reflected ultrasound and outputs reflected ultrasound detection signals.

It should be noted that, in a case where the above-mentioned light guide means is coupled to the probe 11, end portions of the light guide means, such as tip portions of a plurality of optical fibers, are arranged along the direction in which the ultrasound transducers are arranged, and the laser light is outputted toward the subject from each end portion. In the following description, the case where the light guide means is coupled to the probe 11 as described above is described as an example.

To obtain a photoacoustic image or an ultrasound image of the subject, the probe 11 is moved along a direction that is almost perpendicular to the one-dimensional direction in which the ultrasound transducers are arranged, thereby achieving two-dimensional scanning of the subject with the laser light and the ultrasound. This scanning may be achieved by moving the probe 11 manually by the operator, or more precise two-dimensional scanning may be achieved using a scanning mechanism.

The ultrasound unit 12 includes a receiver circuit 21, an AD conversion means 22, a reception memory 23, a data separation means 24, an image reconstruction means 25, a detection and logarithmic conversion means 26, and an image construction means 27. Output from the image construction means 27 is inputted to the image display means 14, which is faulted by a CRT or a liquid crystal display device, for example. The ultrasound unit 12 also includes a transmission control circuit 30, and a control means 31 that controls operations of the components, etc., of the ultrasound unit 12.

The receiver circuit 21 receives the photoacoustic wave detection signals and the reflected ultrasound detection signals outputted from the probe 11. The AD conversion means 22 is a sampling means, which samples the photoacoustic wave detection signals and the reflected ultrasound detection signals received by the receiver circuit 21, and converts the signals into photoacoustic data and reflected ultrasound data, respectively, which are digital signals. This sampling is performed at a predetermined sampling cycle synchronously with an externally-inputted AD clock signal, for example.

The laser light source unit 13 includes a Q-switched pulsed laser 32, which is formed by a Ti:Sapphire laser, an OPO (optical parametric oscillation) laser formed by a YAG laser with second harmonic pumping, an alexandrite laser, or the like, and a flashlamp 33, which is an pumping light source. To the laser light source unit 13, a light trigger signal that instructs to output light is inputted from the control means 31. In response to the light trigger signal, the laser light source unit 13 turns on the flashlamp 33 to pump the Q-switched pulsed laser 32. When the Q-switched pulsed laser 32 is sufficiently pumped by the flashlamp 33, for example, the control means 31 outputs a Q-switch trigger signal. In response to the Q-switch trigger signal, the Q-switched pulsed laser 32 turns on the Q-switch to output pulsed laser light having a wavelength of 756 nm.

The time taken for the Q-switched pulsed laser 32 to be sufficiently pumped after the flashlamp 33 is turned on can be estimated from characteristics, etc., of the Q-switched pulsed laser 32. It should be noted that, in place of controlling the Q-switch by the control means 31 as described above, the Q-switch may be turned on by the laser light source unit 13 after the Q-switched pulsed laser 32 is sufficiently pumped. In this case, a signal indicating that the Q-switch has been turned on may be sent to the ultrasound unit 12.

The control means 31 inputs to the transmission control circuit 30 an ultrasound trigger signal that instructs to transmit ultrasound. In response to the ultrasound trigger signal, the transmission control circuit 30 causes the probe 11 to transmit ultrasound. The control means 31 first outputs the light trigger signal, and then outputs the ultrasound trigger signal. When the light trigger signal is outputted, the laser light is outputted toward the subject and the photoacoustic waves are detected. Then, when the ultrasound trigger signal is outputted, the ultrasound is transmitted to the subject and the reflected ultrasound is detected.

Further, the control means 31 outputs to the AD conversion means 22 a sampling trigger signal that instructs to start sampling. The sampling trigger signal is outputted after the light trigger signal is outputted and before the ultrasound trigger signal is outputted, or more preferably at timing when the laser light is actually outputted toward the subject. To this end, the sampling trigger signal is outputted synchronously with the output of the Q-switch trigger signal by the control means 31, for example. In response to the sampling trigger signal, the AD conversion means 22 starts sampling of the photoacoustic wave detection signals outputted from the probe 11 and received by the receiver circuit 21.

After outputting the light trigger signal, the control means 31 outputs the ultrasound trigger signal at timing when the detection of the photoacoustic waves ends. At this time, the AD conversion means 22 does not stop the sampling of the photoacoustic wave detection signals and continues the sampling. In other words, the control means 31 outputs the ultrasound trigger signal while the AD conversion means 22 continues the sampling of the photoacoustic wave detection signals. As the probe 11 transmits ultrasound in response to the ultrasound trigger signal, the object to be detected by the probe 11 is changed from the photoacoustic waves to the reflected ultrasound. The AD conversion means 22 continues sampling to sample the detected ultrasound detection signals, thereby continuously sampling the photoacoustic wave detection signals and the reflected ultrasound detection signals.

The AD conversion means 22 stores in the common reception memory 23 the photoacoustic data and the reflected ultrasound data obtained by the sampling. The sampled data stored in the reception memory 23 is the photoacoustic data until a certain point of time, and is the reflected ultrasound data after the certain point of time. The data separation means 24 separates the photoacoustic data and the reflected ultrasound data stored in the reception memory 23 from each other.

Now, generation and display of a photoacoustic image are described. To the data separation means 24 shown in FIG. 1, the photoacoustic data obtained by outputting the pulsed laser light having a wavelength of 756 nm toward the subject and the reflected ultrasound data, which are read out from the reception memory 23, are inputted. When a photoacoustic image is generated, the data separation means 24 inputs only the photoacoustic data to the image reconstruction means 25. The image reconstruction means 25 reconstructs data representing a photoacoustic image based on the photoacoustic data.

The detection and logarithmic conversion means 26 generates an envelope of the data representing a photoacoustic image, and then applies logarithmic conversion to the envelope to increase the dynamic range. The detection and logarithmic conversion means 26 inputs the processed data to the image construction means 27. Based on the inputted data, the image construction means 27 constructs a photoacoustic image about a cross section scanned with the pulsed laser light, and inputs the data representing the photoacoustic image to the image display means 14 via the correcting means 51. As a result, the photoacoustic image about the cross section is displayed on the image display means 14.

When there is no particular necessity for correction, the correcting means 51 inputs the data representing the photoacoustic image to the image display means 14 without processing the data. In a case where an instruction is given when it is desired to avoid the near-surface part of the subject appearing on the image display means 14, the correcting means 51 performs correction processing. The correction processing will be described in detail later.

It should be noted that, as described previously, the subject may be two-dimensionally scanned with the laser light by moving the probe 11, and a photoacoustic image that three-dimensionally displays a desired part, such as blood vessels, of the subject may be generated and displayed based on image data about a plurality of cross sections obtained by the two-dimensional scanning.

Further, an ultrasound image of the subject may be generated and displayed based on the reflected ultrasound data separated by the data separation means 24. The generation and display of the ultrasound image may be performed according to a conventionally known method, which is not directly related to the invention and therefore is not described in detail. The ultrasound image and the photoacoustic image may be displayed with being superimposed one on the other.

It should be noted that, although ultrasound is used as the acoustic wave outputted toward the subject to obtain a reflected ultrasound image in this embodiment, the acoustic wave is not limited to ultrasound. The acoustic wave may be one having an audible frequency, as long as the frequency is appropriately selected depending on the subject, measurement conditions, etc.

In a case where a photoacoustic image of blood vessels, or the like, at a position deeper than the surface of the subject is generated and displayed, it is necessary to set a high light intensity so that the laser light outputted from the laser light source unit 13 reaches the deeper position in the subject. In this case, however, near-surface parts of the subject (such as the epidermis and the body hair) exposed to the laser light emit photoacoustic waves, and a photoacoustic image of the near-surface parts may often be generated and displayed. In a case where the deep part, which is the intended part to be observed, is displayed with increased luminance, part of the displayed image is saturated, and the displayed near-surface parts may hinder observation of the blood vessels, which are the intended part to be observed. Further, in a case where a projection image is displayed, the displayed near-surface parts may hide the part to be observed located behind the near-surface parts. The photoacoustic imaging device 10 of this embodiment allows solving this problem. Now, this point is described in detail.

As shown in FIG. 1, the data separation means 24 is connected to a region detection means 50, and the photoacoustic data outputted from the data separation means 24 is also inputted to the region detection means 50. The region detection means 50 detects a near-surface region of the subject based on the inputted photoacoustic data. It should be noted that, although the near-surface region is detected based on the digitized photoacoustic data in this embodiment, the near-surface region can be detected based on the photoacoustic wave detection signals before digitized. In the invention, "detecting a near-surface region based on the photoacoustic wave detection signals" encompasses detecting the near-surface region of the subject based on the photoacoustic data resulting from digitizing the photoacoustic wave detection signals.

Figure 2:
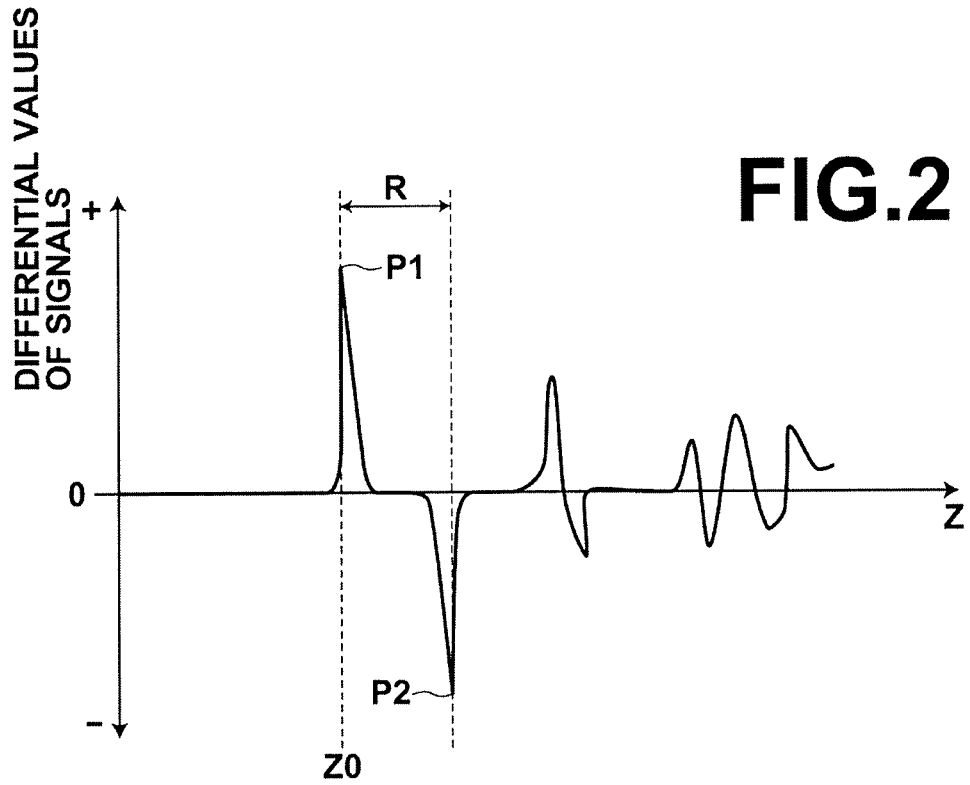
FIG. 2 is a schematic diagram for explaining one method for detecting a near-surface region of a subject with the device shown in FIG. 1.

Now, a specific procedure for detecting the near-surface region is described with reference to FIG. 2. First, the region detection means 50 differentiates the photoacoustic data for each linear region that extends from the surface of the subject toward the depth direction (which refers to a direction in which the depth increases) of the subject. Values of this photoacoustic data correspond to values of the photoacoustic wave detection signals, and indicates intensities of the photoacoustic waves. FIG. 2 shows an example of distribution of the differential values, where "Z" denotes the depth direction. As shown, the distribution of the differential values along the depth direction Z has clear extrema P1 and P2 at the front side and the back side, respectively, of the skin tissue (of the epidermis, or the epidermis plus the upper dermis, for example) of the subject. Therefore, the region detection means 50 detects a position Z0 where the first extremum P1 of the differential values toward the depth direction is found as the boundary between the subject and the air, i.e., the position of the surface of the subject, and detects a region R extending from the position Z0 to a position where the next extremum P2 is found as the near-surface region.

Figure 7:
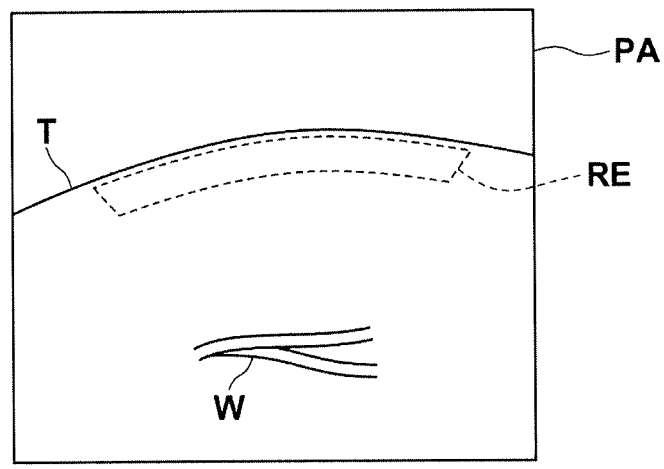
FIG. 7 is a schematic diagram for explaining the near-surface region detected with the device shown in FIG. 1.

In a case where a photoacoustic image about a certain cross section of the subject is generated and displayed, the region detection is performed at a plurality of positions along the cross section, and a two-dimensional near-surface region is detected. An example of the two-dimensional near-surface region is schematically shown in FIG. 7. In FIG. 7, "PA" denotes a photoacoustic image, "T" denotes the surface of the subject, "W" denotes the part to be observed in the interior of the subject, and "RE" denotes the two-dimensional near-surface region.

The region detection means 50 inputs information of the thus found near-surface region RE to the correcting means 51 shown in FIG. 1. The correcting means 51 removes, from the image data representing the photoacoustic image outputted from the image construction means 27, image information representing the near-surface region RE indicated by the above information, and appropriately interpolates the removed part. Then, the correcting means 51 inputs the resulting image data to the image display means 14. On the image display means 14, the near-surface part of the subject is not displayed, and a photoacoustic image that basically shows only the part to be observed W is displayed.

It should be noted that, in place of completely removing the image information about the near-surface region RE, as described above, attenuation processing for reducing the display luminance of the near-surface region RE may be performed. In this case, a thin image of the near-surface part of the subject is displayed in the display image. Even in this case, the troublesome situation where discrimination of the part to be observed is difficult due to the displayed near-surface part can be prevented, when compared to a case where the near-surface part is clearly displayed. In the invention, "attenuating information of the near-surface region when . . . is displayed" encompasses displaying an image with completely removing the information of the near-surface region, as described above. In the case where the attenuation processing as described above is performed, it is preferred to display an image with enclosing the region RE by a dashed line or a solid line, as shown in FIG. 7, to indicate the position of the processed near-surface region RE.

Further, in a case where a photoacoustic image is generated and displayed as a so-called 3D image display that shows a pseudo three-dimensional presentation of the part to be observed of the subject, a three-dimensional near-surface region, which is a set of two-dimensional near-surface regions, as described above, can be detected. In such a 3D image, the part to be observed, such as blood vessels, at a deep position may be covered by parts of skin in the near-surface region depending on the angle of display. In this case, observation of the intended part to be observed cannot be achieved. Applying the invention to such a case allows obtaining a particularly high level of effect of improving diagnosis performance of a photoacoustic image.

Figure 3:
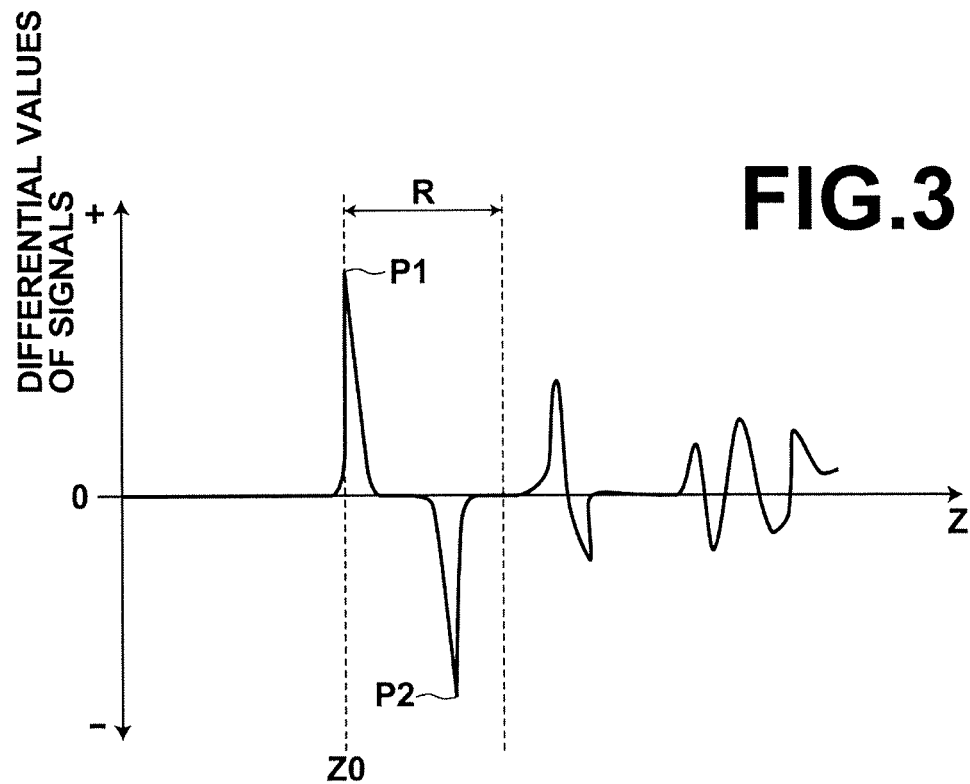
FIG. 3 is a schematic diagram for explaining another method for detecting the near-surface region of the subject with the device shown in FIG. 1.

Next, another method for detecting the near-surface region RE is described with reference to FIG. 3. It should be noted that the curve shown in FIG. 3 is the same as that shown in FIG. 2, and other elements denoted by the same symbols as those in FIG. 2 are the same elements as those shown in FIG. 2. This method may be performed by the region detection means 50 shown in FIG. 1. The position Z0 where the first extremum P1 of the differential values toward the depth direction is found is detected as the boundary between the subject and the air, i.e., the position of the surface of the subject, and the region detection means 50 detects a region R extending between the position Z0 and a position apart from the position Z0 by a predetermined length in the depth direction of the subject as the near-surface region.

The predetermined length is preferably defined by the number of pixels, such as 400 pixels. A preferred length for the predetermined length can be found experimentally or empirically. It is desirable that the predetermined length be changeable, as appropriate, according to an instruction inputted by the user of the device. This allows the user of the device to set an optimal thickness of the near-surface region for attenuating the display information while observing the photoacoustic image displayed on the image display means 14.

Figure 4:
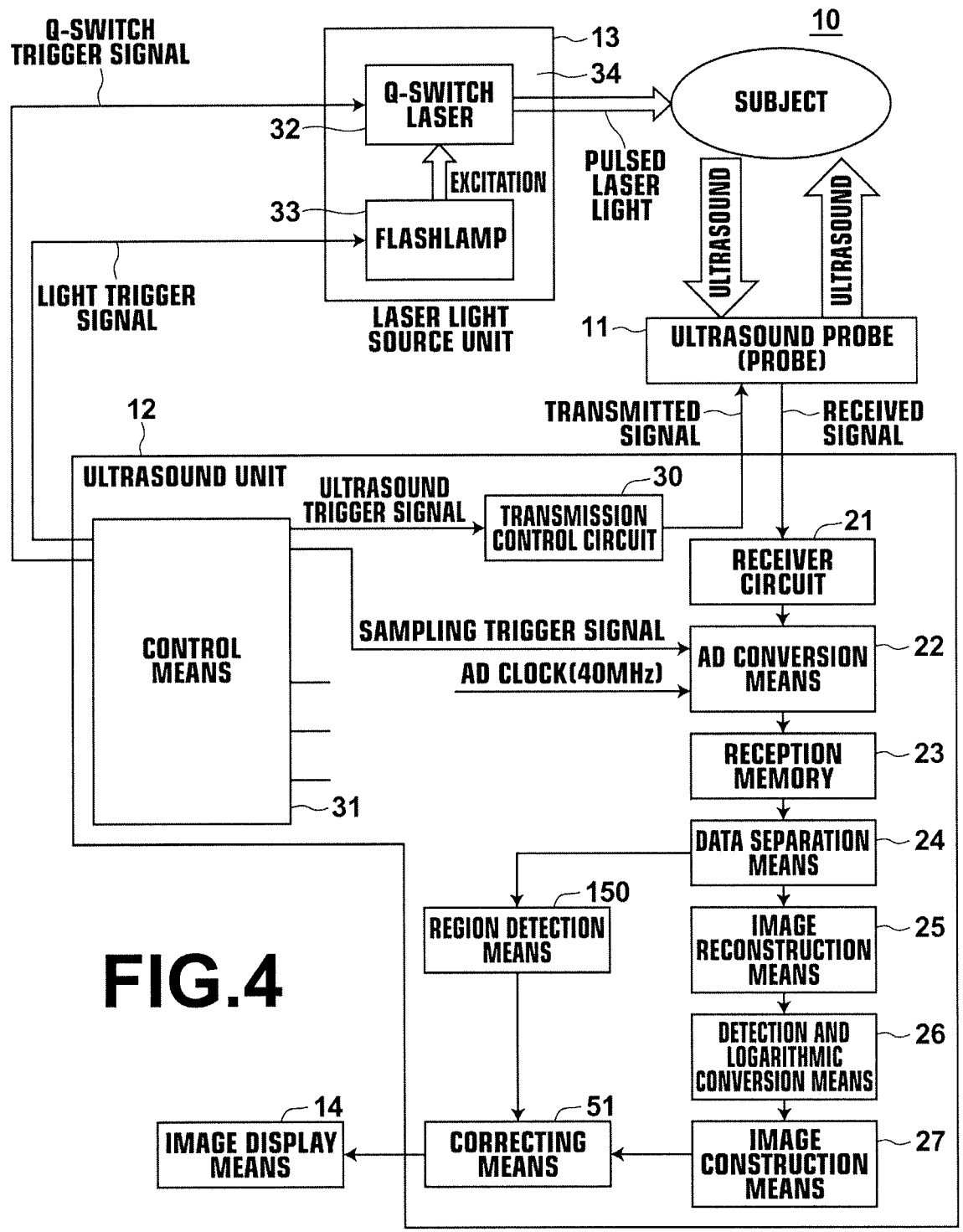
FIG. 4 is a block diagram illustrating the schematic configuration of a photoacoustic imaging device according to another embodiment of the invention.

Next, another embodiment of the invention is described with reference to FIG. 4. In FIG. 4, elements that are equivalent to the elements shown in FIG. 1 are denoted by the same reference numerals, and explanations thereof are omitted unless otherwise necessary (the same applies hereinafter).

In the device shown in FIG. 4, a region detection means 150 that detects the near-surface region from the digital reflected ultrasound data outputted from the data separation means 24 is applied, in place of the region detection means 50 shown in FIG. 1. The region detection means 150 first calculates moving average values of values of the reflected ultrasound data along the depth direction from the surface of the subject (which correspond to moving average values of signal intensities of the reflected ultrasound detection signals along the same direction). The values of the reflected ultrasound data have reduced influence of specifications that is unique to ultrasound, and indicates an interfacial boundary based on intensities of the reflected ultrasound reflected from the subject.

Figure 5:
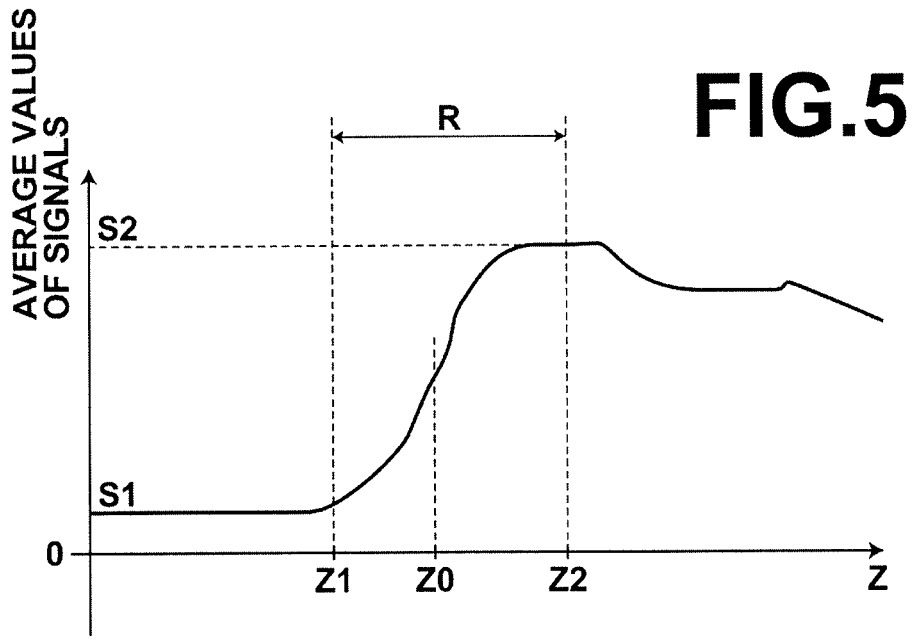
FIG. 5 is a schematic diagram for explaining one method for detecting the near-surface region of the subject with the device shown in FIG. 4.

FIG. 5 shows an example of distribution of the average values, where "Z" denotes the depth direction. As shown, the distribution of the average values along the depth direction Z has a minimum value S1 for a gel or water area outside the surface of the subject, and the value begins to increase from the minimum value S1 at a position Z1 of the surface of the subject. The value gradually increases for an area where the skin tissue is present, and begins to decrease for an area where the skin tissue is no longer present. That is, a local maximum value S2 of the average values is found at a position Z2 around which the skin tissue is no longer present. Therefore, the region detection means 150 detects a region R extending between the position Z1 and the position Z2 as the near-surface region. It should be noted that the local maximum value S2 is distributed over a certain range of depth, and the position Z2 may be set at any position within the range of depth.

Figure 8:
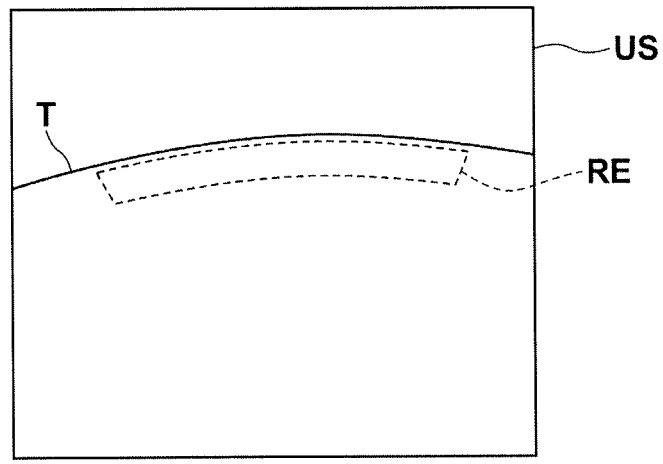
FIG. 8 is a schematic diagram for explaining the near-surface region detected with the device shown in FIG. 4.

In a case where a photoacoustic image about a certain cross section of the subject is generated and displayed, the region detection is performed at a plurality of positions along the cross section, and a two-dimensional near-surface region is detected. An example of the two-dimensional near-surface region is schematically shown in FIG. 8. In FIG. 8, "US" denotes an ultrasound image, "T" denotes the surface of the subject, and "RE" denotes the two-dimensional near-surface region.

The region detection means 150 inputs information of the thus found near-surface region RE to the correcting means 51 shown in FIG. 4. The correcting means 51 removes, from the image data representing the photoacoustic image outputted from the image construction means 27, image information representing the near-surface region RE indicated by the above information, and appropriately interpolates the removed part. Then, the correcting means 51 inputs the resulting image data to the image display means 14. On the image display means 14, the near-surface part of the subject is not displayed, and a photoacoustic image that basically shows only the part to be observed W is displayed.

Also in this case, in place of completely removing the image information about the near-surface region RE, as described above, attenuation processing for reducing the display luminance of the near-surface region RE may be performed. In this case, a thin image of the near-surface part of the subject is displayed in the display image. Even in this case, the troublesome situation where discrimination of the part to be observed is difficult due to the displayed near-surface part can be prevented, when compared to a case where the near-surface part is clearly displayed.

Figure 6:
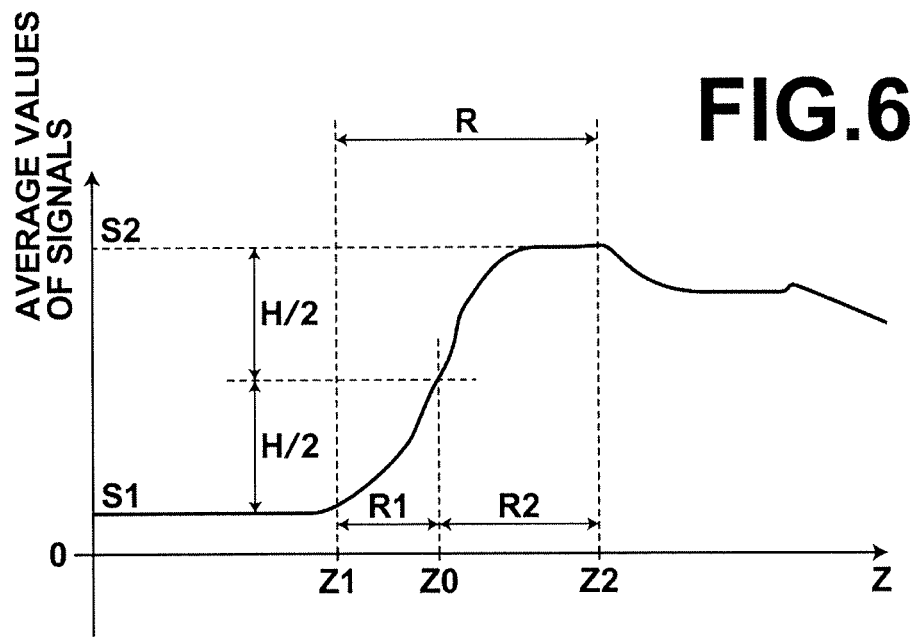
FIG. 6 is a schematic diagram for explaining another method for detecting the near-surface region of the subject with the device shown in FIG. 4.

Next, another method for detecting the near-surface region RE from the reflected ultrasound data is described with reference to FIG. 6. It should be noted that the curve shown in FIG. 6 is the same as that shown in FIG. 5, and other elements denoted by the same symbols as those in FIG. 5 are the same elements as those shown in FIG. 5. This method may be performed by the region detection means 150 shown in FIG. 4. The region detection means 150 calculates an average value between the minimum value S1 and the local maximum value S2 of the average values of the reflected ultrasound data, and finds a position Z2 apart from a position Z0 where the calculated average value is found by a predetermined length R2 in the depth direction of the subject and a position Z1 apart from the position Z0 by a predetermined length R1 in the opposite direction from the depth direction of the subject. Then the region detection means 150 detects a region extending between the position Z2 and the position Z1 as the near-surface region R.

The predetermined lengths R2 and R1 are preferably defined by the numbers of pixels, such that the former is 300 pixels and the latter is 100 pixels. Preferred lengths for the predetermined lengths R2 and R1 can be found experimentally or empirically. It is desirable that the predetermined lengths be changeable, as appropriate, according to an instruction inputted by the user of the device. This allows the user of the device to set an optimal thickness of the near-surface region for attenuating the display information while observing the photoacoustic image displayed on the image display means 14.

Figure 10:
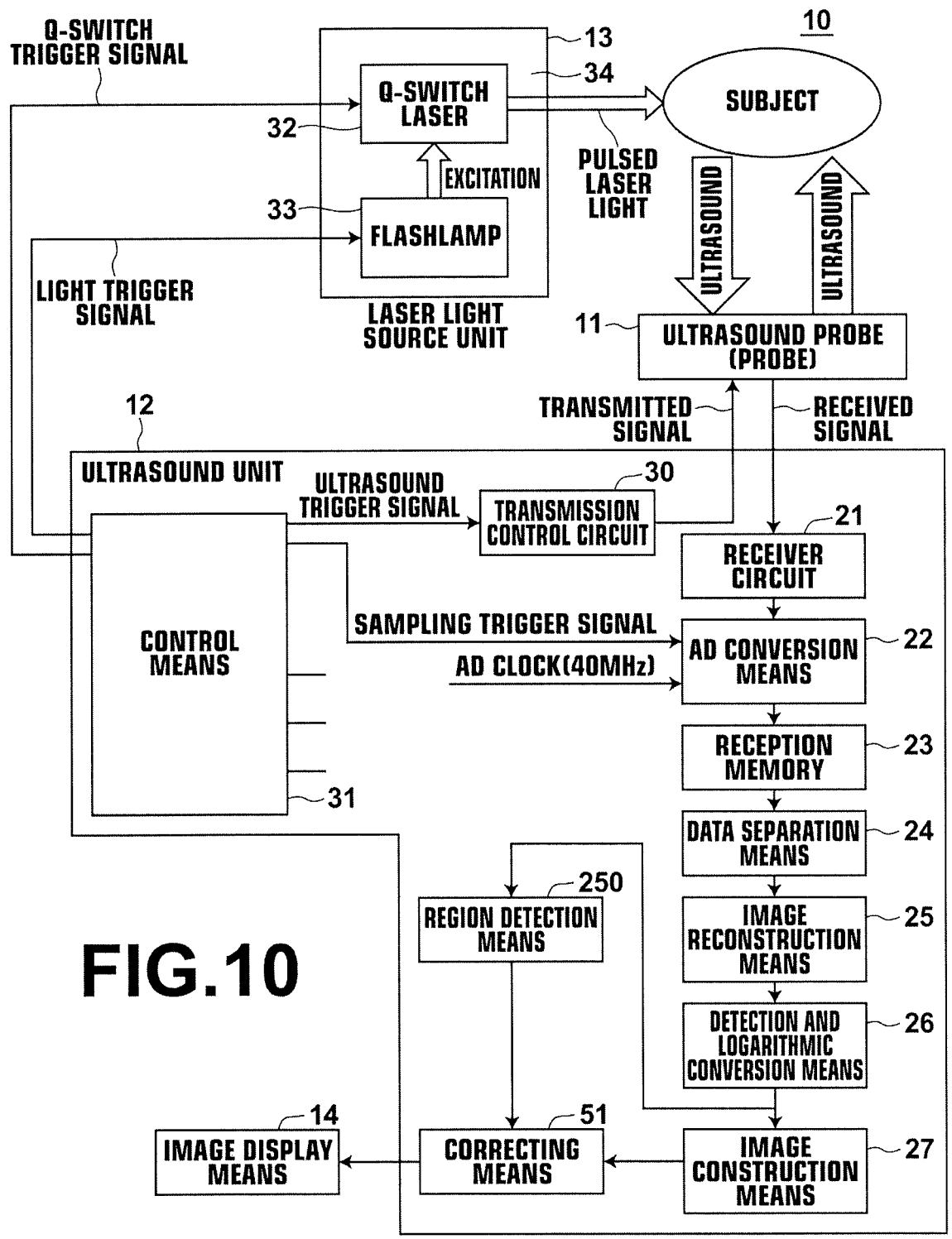
FIG. 10 is a block diagram illustrating the schematic configuration of a photoacoustic imaging device according to yet another embodiment of the invention.

Next, yet another embodiment of the invention is described with reference to FIG. 10. In the device shown in FIG. 10, a region detection means 250 is applied, in place of the region detection means 50 shown in FIG. 1. The region detection means 250 detects the near-surface region from the digital photoacoustic data having been subjected to the logarithmic conversion, which is outputted from the detection and logarithmic conversion means 26. Now, region detection processing, correction processing, etc., performed by the region detection means 250 and the following means are described with reference to FIG. 11, which shows the flow of the processing.

As the processing is started, the region detection means 250 first substitutes data values that are not greater than a predetermined threshold value of the photoacoustic data outputted from the detection and logarithmic conversion means 26 with zero value, in step S1. More specifically, in a case where the photoacoustic data before the logarithmic conversion is resulted from sampling at a sampling frequency of 40 MHz and a quantization bit rate of 12 bits, and the digital photoacoustic data after the logarithmic conversion has values ranging from 1 to 11, for example, the threshold value is set to around "4". This processing removes noise components in the low luminance range.

Then, in step S2, the region detection means 250 applies smoothing processing to the photoacoustic data. Specifically, the smoothing processing is achieved by calculating a moving average for each set of 21 points of the photoacoustic data in the depth direction of the subject. Namely, for photoacoustic data of a given pixel, an average value of photoacoustic data of 21 pixels including continuous 10 pixels from the given pixel toward the shallower side of the subject, continuous 10 pixels from the given pixel toward the deeper side of the subject, and the given pixel is calculated, and the calculated average value is used as the photoacoustic data of the given pixel, thereby achieving the smoothing processing.

Then, in step S3, the region detection means 250 applies differential processing to the smoothed photoacoustic data. As described previously, the differential processing is performed for photoacoustic data of each linear region that extends from the surface of the subject toward the depth direction Z. FIG. 12 shows an example of distribution of differential values resulting from the differential processing, in the same manner as in FIG. 2. As shown in FIG. 12, the distribution of differential values may include noise components N at positions on the light source side of the surface of the subject (in the opposite direction from the depth direction Z). In the case where a position where the first extremum P1 of the differential values toward the depth direction Z is found is detected as the surface of the subject position, as in the method explained using FIG. 2, if there are the noise components N, the noise components N may cause a situation where a position where an extremum of the noise components N is found is incorrectly detected as the surface of the subject position.

In this embodiment, such an incorrect detection is prevented. Namely, in step S4, the region detection means 250 applies smoothing processing to the differentiated photoacoustic data by calculating a moving average for each set of 11 points in the depth direction, for example, and then detects the surface position of the subject based on a predetermined threshold value in step S5. This detection of the surface position is achieved by regarding a position Z0 where a differential value that first exceeds a predetermined threshold value Th is found, which is detected with respect to a line toward the depth direction Z, as the boundary between the subject and an ultrasound coupler or an ultrasound gel, i.e., the surface position of the subject. This detection of the surface position is performed for a plurality of lines (for example, every line) toward the depth direction Z.

Then, in step S6, the region detection means 250 detects a region R extending between the position Z0 and a position apart from the position Z0 by a predetermined length in the depth direction of the subject as the near-surface region, and the correcting means 51 deletes image data about the near-surface region from the image data carrying the photoacoustic image sent from the image construction means 27. Then, in step S7, the correcting means 51 adjusts luminance and contrast so that diagnosis performance is not impaired after the deletion of image data. Further, in a case where a composite image of the above-described ultrasound image and the photoacoustic image is displayed, the correcting means 51 adjusts a color map showing each image portion, and the resulting photoacoustic image is displayed on the image display means 14 in step S8.

Also in this embodiment, image data about the near-surface region of the subject is deleted from the image data carrying a photoacoustic image, as described above. Therefore, a photoacoustic image of the near-surface part is not generated and displayed, thereby allowing displaying a photoacoustic image where an intended part to be observed, such as blood vessels, is more visible.

It should be noted that a preferable value for the threshold value Th can be found experimentally or empirically. As one example, in the case where the photoacoustic data before the logarithmic conversion is resulted from sampling at a sampling frequency of 40 MHz and a quantization bit rate of 12 bits, and the digital photoacoustic data after the logarithmic conversion has values ranging from 1 to 11, as described previously, the threshold value Th may be set to "0.02", for example. Also, a preferable value for the width of the region R for deleting the image data can be found experimentally or empirically. As one example, the width of the region R may be set to correspond to 130 pieces of data.

Although the region R extending across a predetermined length in the depth direction of the subject is detected as the near-surface region in this embodiment, a position where the next extremum P2 toward the depth direction is found after the first extremum P1 of the differential values is found may be detected as the back side of a skin tissue, or the like, of the subject, and a region extending between a position where a differential value that exceeds the threshold value Th is found and the position where the extremum P2 is found may be detected as the near-surface region.

Further, in this embodiment, the smoothing processing applied to the photoacoustic data in step S2 shown in FIG. 11 and the smoothing processing applied to the differential data in step S4 allow preventing incorrect detection of the near-surface region due to noise components in each data.

It should be noted that, in order to prevent incorrect detection of the surface position of the subject due to the noise components N as shown in FIG. 12, it is also effective to detect, as the surface position of the subject, a position where the first extremum P1 toward the depth direction is found after a differential value that exceeds the predetermined threshold value Th is found. Also in this case, a region R extending across a predetermined length in the depth direction of the subject from the position where the extremum P1 is found may be detected as the near-surface region, or a range extending between the position where the extremum P1 is found and the position where the next extremum P2 in the depth direction is found may be detected as the near-surface region.

It should be noted that the photoacoustic imaging device and method of the invention are not limited to the above-described embodiments, and various modifications and changes made to the above-described embodiments are also within the scope of the invention.

Figure 9:
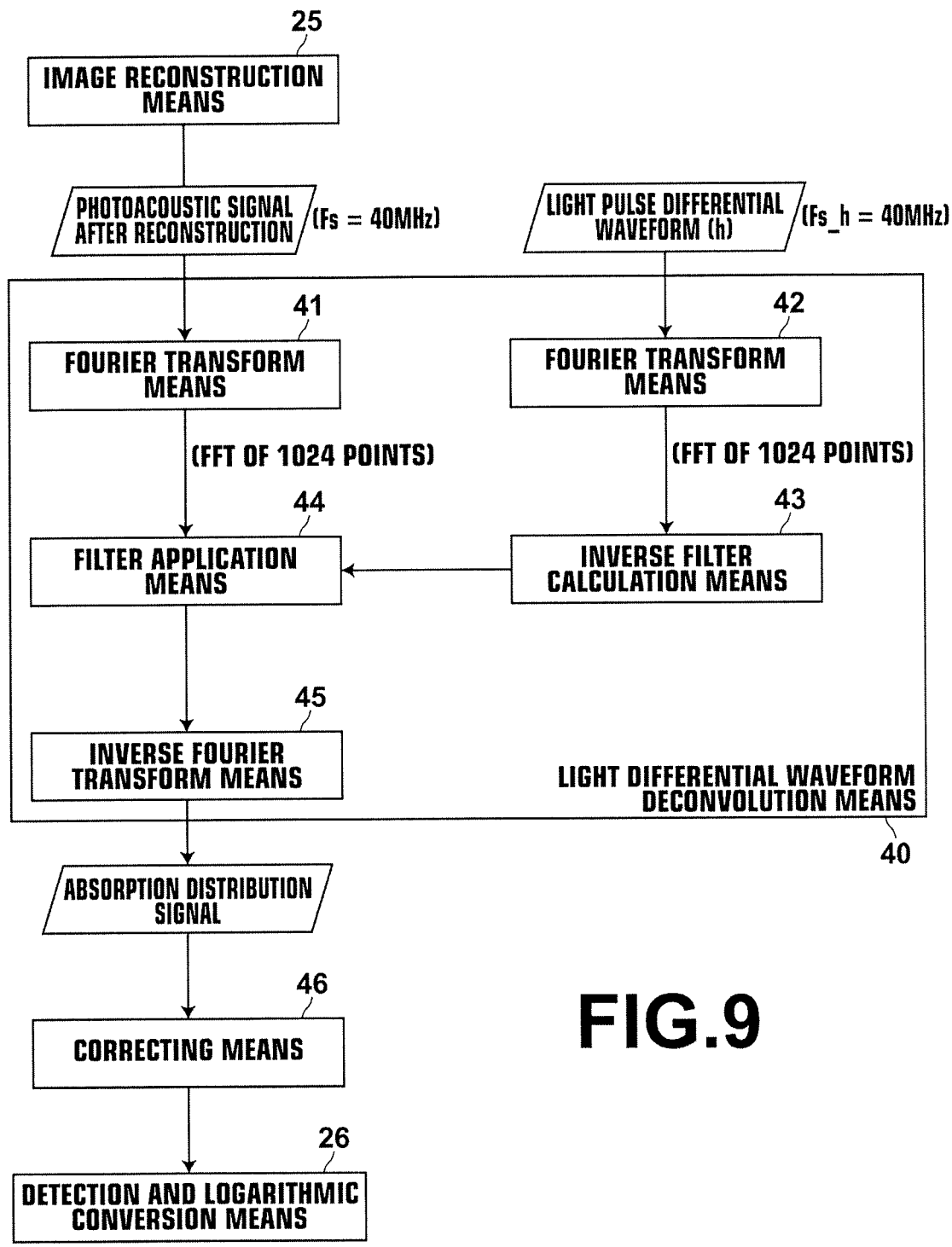
FIG. 9 is a block diagram illustrating part of the configuration of a photoacoustic imaging device according to still another embodiment of the invention.

For example, the invention is also applicable to a photoacoustic imaging device and a photoacoustic imaging method where deconvolution processing is performed. FIG. 9 is a block diagram illustrating part of a photoacoustic imaging device configured to perform deconvolution processing. The configuration shown in FIG. 9 is inserted between the image reconstruction means 25 and the detection and logarithmic conversion means 26 shown in FIG. 1, for example, and includes a light differential waveform deconvolution means 40 and a correcting means 46 connected downstream the light differential waveform deconvolution means 40. The light differential waveform deconvolution means 40 includes Fourier transform means 41 and 42, an inverse filter calculation means 43, a filter application means 44, and an inverse Fourier transform means 45.

The light differential waveform deconvolution means 40 deconvolves, from the data representing a photoacoustic image outputted from the image reconstruction means 25, a light pulse differential waveform obtained by differentiating a temporal waveform of light intensity of the pulsed laser light outputted toward the subject. With this deconvolution, photoacoustic image data representing an absorption distribution is obtained.

Now, this deconvolution is described in detail. The Fourier transform means (first Fourier transform means) 41 of the light differential waveform deconvolution means 40 converts the reconstructed photoacoustic image data from the time domain signal into a frequency domain signal by applying a discrete Fourier transform. The Fourier transform means (second Fourier transform means) 42 converts a signal obtained by sampling the light pulse differential waveform at a predetermined sampling rate from the time domain signal into a frequency domain signal by applying a discrete Fourier transform. As an algorithm for the Fourier transform, FFT can be used, for example.

In this embodiment, the sampling rate for sampling the light pulse differential waveform is the same as the sampling rate for sampling the photoacoustic wave detection signals at the AD conversion means 22. For example, the photoacoustic wave detection signals are sampled synchronously with a sampling clock of Fs=40 MHz, and the light pulse differential waveform is also sampled at a sampling rate of Fs_h=40 MHz. The Fourier transform means 41 applies a Fourier transform of 1024 points, for example, to the photoacoustic image data obtained by the sampling at 40 MHz and outputted from the image reconstruction means 25. The Fourier transform means 42 applies a Fourier transform of 1024 points to the light pulse differential waveform sampled at 40 MHz.

The inverse filter calculation means 43 calculates a reciprocal of the Fourier transformed light pulse differential waveform as an inverse filter. For example, the inverse filter calculation means 43 calculates, as the inverse filter, conj (fft_h)/abs(fft_h)$^2$, where fft_h is a signal obtained by Fourier transforming a light pulse differential waveform h. The filter application means 44 applies the inverse filter calculated by the inverse filter calculation means 43 to the photoacoustic image data Fourier transformed by the Fourier transform means 41. For example, the filter application means 44 multiplies, for each element, the Fourier coefficient of the photoacoustic image data by the Fourier coefficient of the inverse filter. By applying the inverse filter, the light pulse differential waveform is deconvolved from the frequency domain signal. The inverse Fourier transform means 45 converts the photoacoustic signal processed with the inverse filter from the frequency domain signal to a time domain signal using an inverse Fourier transform. By applying the inverse Fourier transform, a time domain absorption distribution signal is obtained.

By performing the above-described processing, a light differential term can be removed from the photoacoustic wave detection signal in which the light differential term is convolved, thereby allowing calculating an absorption distribution from the photoacoustic wave detection signal. By imaging such an absorption distribution, a photoacoustic image representing an absorption distribution image can be obtained.

The correcting means 46 corrects the data from which the light pulse differential waveform has been deconvolved to remove influence of reception angle-dependent properties of the ultrasound transducers of the probe 11 from the data from which the light pulse differential waveform has been deconvolved. In addition to or in place of the reception angle-dependent properties, the correcting means 46 removes influence of an incoming light distribution on the subject from the data from which the light pulse differential waveform has been deconvolved. It should be noted that a photoacoustic image may be generated without performing these corrections.

What is claimed is:

1. A photoacoustic imaging device comprising:
 a light source that emits light toward a part to be observed in a subject through a surface of the subject;
 a photoacoustic wave detection unit that obtains photoacoustic wave detection signals by detecting photoacoustic waves emitted from the part to be observed exposed to the light;
 an image display that displays the part to be observed; and
 a controller configured to:
  perform image processing on the part to be observed based on the photoacoustic wave detection signals;
  detect a near-surface region of the subject based on a set of the photoacoustic wave detection signals with respect to a depth direction of the subject;
  perform attenuation processing of information of the near-surface region when the part to be observed is displayed;
  detect the photoacoustic wave detection signals with respect to a region extending from the surface of the subject toward the depth direction of the subject;
  calculate differential values of the photoacoustic wave detection signals;
  determine a first extremum of the differential values; and
  determine where a differential value of the photoacoustic wave detection signal exceeds a first predetermined threshold value,
 wherein the detected near-surface region is a region extending between a position where a first extremum of differential values of the photoacoustic wave detection signals is found after a differential value of the photoacoustic wave detection signal that first exceeds the predetermined threshold value is found and a position where a second extremum of the differential values is found,
 wherein the position of the second extremum is further apart from the surface of the subject than the position of the first extremum, and
 wherein the first extremum is a local maximal and the second extremum is a local minimum.

2. The photoacoustic imaging device as claimed in claim 1, wherein the controller is further configured to perform smoothing processing to the photoacoustic wave detection signals before the differential values of the photoacoustic wave detection signals are calculated.

3. The photoacoustic imaging device as claimed in claim 1, the controller is further configured to perform smoothing processing to the differential values used in processing for detecting the near-surface region before the processing for detecting the near-surface region is performed.

4. A photoacoustic imaging device comprising:
 a light source that emits light toward a part to be observed in a subject through a surface of the subject;
 a photoacoustic wave detection unit that obtains photoacoustic wave detection signals by detecting photoacoustic waves emitted from the part to be observed exposed to the light;
 an image display that displays the part to be observed; and
 a controller configured to:
  perform image processing on the part to be observed based on the photoacoustic wave detection signals;
  detect a near-surface region of the subject based on a set of the photoacoustic wave detection signals with respect to a depth direction of the subject;
  perform attenuation processing of information of the near-surface region when the part to be observed is displayed;
  detect the photoacoustic wave detection signals with respect a region extending from the surface of the subject toward the depth direction of the subject;
  calculate differential values of the photoacoustic wave detection signals;
  determine a first extremum of the differential values; and
  determine where a differential value of the photoacoustic wave detection signal exceeds a first predetermined threshold value,
 wherein the detected near-surface region is a region extending between a position where the first extremum of differential values of the photoacoustic wave detection signals is found after the differential value of the photoacoustic wave detection signal that first exceeds the predetermined threshold value is found and a position of the subject apart from the position where the first extremum is found by a predetermined length in the depth direction of the subject.

5. The photoacoustic imaging device as claimed in claim 1, wherein the controller is further configured to perform smoothing processing to the photoacoustic wave detection signals before the differential values of the photoacoustic wave detection signals are calculated.

6. The photoacoustic imaging device as claimed in claim 4, wherein the controller is further configured to perform smoothing processing to the differential values used in processing for detecting the near-surface region before the processing for detecting the near-surface region is performed.

\* \* \* \* \*